(12) United States Patent
Martinez (10) Patent No.: US 9,908,655 B2
(45) Date of Patent: Mar. 6, 2018

(54) STYLUS WINDING FIXTURE FOR WINDING SURGICAL SUTURES AND METHOD OF WINDING A SUTURE

(71) Applicant: Ethicon, Inc., Somerville, NJ (US)

(72) Inventor: Joel Manuel Martinez, Caguas, PR (US)

(73) Assignee: Ethicon, Inc., Somerville, NJ (US)

( * ) Notice: Subject to any disclaimer, the term of this patent is extended or adjusted under 35 U.S.C. 154(b) by 442 days.

(21) Appl. No.: 14/699,292

(22) Filed: Apr. 29, 2015

(65) Prior Publication Data

US 2016/0317148 A1  Nov. 3, 2016

(51) Int. Cl.
| | |
|---|---|
| B65B 63/04 | (2006.01) |
| B65H 54/44 | (2006.01) |
| A61B 17/06 | (2006.01) |
| B65B 35/26 | (2006.01) |
| B65B 43/60 | (2006.01) |
| B65H 54/02 | (2006.01) |
| A61B 17/00 | (2006.01) |

(52) U.S. Cl.
CPC ........ B65B 63/04 (2013.01); A61B 17/06133 (2013.01); B65B 35/26 (2013.01); B65B 43/60 (2013.01); B65H 54/02 (2013.01); B65H 54/44 (2013.01); *A61B 2017/00526* (2013.01); *A61B 2017/06142* (2013.01)

(58) Field of Classification Search
CPC ...... B65B 363/04; B65H 54/02; B65H 54/44; A61B 17/06114; A61B 17/06133; A61B 2017/06142
USPC ............................ 53/430, 116, 118; 206/63.3
See application file for complete search history.

(56) References Cited

U.S. PATENT DOCUMENTS

| | | | | |
|---|---|---|---|---|
| 2,727,699 | A | * | 12/1955 | Bilane et al. .......... B65H 54/10 242/472.7 |
| 3,618,282 | A | * | 11/1971 | Hagel et al. .............. B65B 5/04 53/116 |
| 4,253,289 | A | * | 3/1981 | Cole et al. .............. B65B 63/06 53/116 |
| 5,469,689 | A | * | 11/1995 | Demarest et al. ................ A61B 17/06133 53/430 |
| 5,473,810 | A | * | 12/1995 | Demarest et al. ................ A61B 17/06133 53/118 |
| 5,491,954 | A | * | 2/1996 | Sobel ............... A61B 17/06133 53/116 |
| 5,660,024 | A | | 8/1997 | Ivanov et al. |
| 5,664,404 | A | | 9/1997 | Ivanov et al. |
| 5,765,343 | A | * | 6/1998 | Whittaker ............... B65B 63/04 53/430 |
| 5,778,510 | A | * | 7/1998 | Negoro et al. ......... G03B 17/26 53/118 |
| 6,047,815 | A | | 4/2000 | Cerwin et al. |
| 6,135,272 | A | | 10/2000 | Sobel et al. |

(Continued)

FOREIGN PATENT DOCUMENTS

DE        1115815 B  * 10/1961  ............. B65H 54/44

*Primary Examiner* — Stephen F Gerrity
(74) *Attorney, Agent, or Firm* — E. Richard Skula (57) ABSTRACT

Novel adaptive stylus winding assemblies for use in winding surgical sutures in tray packages are disclosed. The stylus winding assemblies have a pivotally mounted stylus member and a biasing element to facilitate winding a suture into a suture track of a suture tray. The winding assemblies provide for reliable product supply, quality improvements and cost reductions.

17 Claims, 14 Drawing Sheets

(56) References Cited

U.S. PATENT DOCUMENTS

| | | |
|---|---|---|
| 6,463,719 B2 | 10/2002 | Dey et al. |
| 6,644,469 B2 | 11/2003 | Alpern |
| 6,804,937 B2 | 10/2004 | Dey et al. |
| 8,011,499 B2 | 9/2011 | Karow et al. |
| 2002/0069617 A1* | 6/2002 | Dey et al. ........ A61B 17/06133 53/430 |
| 2004/0177594 A1* | 9/2004 | Dey et al. ........ A61B 17/06133 53/430 |

* cited by examiner

STYLUS WINDING FIXTURE FOR WINDING SURGICAL SUTURES AND METHOD OF WINDING A SUTURE

FIELD OF THE INVENTION

The field of art to which this invention pertains is surgical needles and surgical sutures, more particularly equipment for winding surgical sutures and attached surgical needles into suture packages.

BACKGROUND OF THE INVENTION

Surgical needles and attached surgical sutures are well known in the art. Surgical needles and sutures are packaged in a variety of packages for delivery of the needles and sutures to the surgeon. The packages need to have a number of important characteristics including ease of loading, ease of dispensing, and protection of the needle and suture during handling, sterilization, shipping and storage. Tray-type packages having a peripheral channel for receiving a suture are commonly used to package needles and suture combinations. The tray packages have a number of advantages. For example, the packages are relatively inexpensive to manufacture and are typically molded from biocompatible, inert polymeric materials. The track packages provide excellent protection to the sutures during processing, sterilization, shipment and storage. The packages are easy to handle by the surgical staff, and sutures are easy to withdraw from the tray packages in a consistent manner without tangles or lock-ups. One particular advantage of tray packages is their ease of suture loading in high speed, automated packaging processes. Examples of tray packages are disclosed in U.S. Pat. Nos. 6,135,272, 6,047,815, 6,644,469, and 8,011,499. Tray packages are typically made with moveable doors or members that cover the top of the track to prevent the suture from moving out of the track.

Surgical sutures are packaged in tray packages by using conventional winding fixtures. The fixture typically has a rotatable base with mounting pins. A tray package is mounted on the base and pins such that the top of the tray package is facing upwardly. Then a winding stylus mounted to a winding head directs a length of suture down into a track of the suture tray as the tray rotates so that the suture is placed in the track in a uniform manner. Examples of such winding fixtures and styluses are disclosed in U.S. Pat. Nos. 5,660,024, 5,664,404, 6,804,937, and 6,463,719.

Although conventional winding fixtures and styluses perform adequately for their intended use, there may be deficiencies associated with such winding fixtures. For example, a stylus in a conventional winding fixture is rigidly mounted to the winding fixture and this does not allow for variations in the dimensions of tray packages resulting in potentially improper placement of the sutures in the track of the package. In addition, a stylus is typically engaged with a winding head via a bearing. As the bearing wears with time, the bearing wear may result in loosening of the stylus in the mounting assembly, which may also result in improper suture placement.

There is a need in this art for novel winding styluses for use in automated suture tray winding machines that overcome the deficiencies of the prior art.

SUMMARY OF THE INVENTION

Accordingly, a novel adaptive suture winding stylus is disclosed. The suture winding stylus has a base member. The base member has a top side, a bottom side and opposed front and rear lateral sides. A stylus member is pivotally mounted to the base member. The stylus member has a proximal end, a distal end, a top side and a bottom side. A biasing element is associated with the base member for engaging the stylus member.

Another aspect of the present invention is a suture winding assembly. The suture winding assembly has a nest member for receiving a suture tray package having a winding channel. The assembly has a winding head for rotatably engaging the nest and tray package. The assembly also has a novel adaptive suture winding stylus for engaging the winding head and the tray package. The winding stylus has a base member. The base member has a top side, a bottom side and opposed front and rear lateral sides. A stylus member is pivotally mounted to the base member. The stylus member has a proximal end, a distal end, a top side and a bottom side. A biasing element is associated with the base member for engaging the stylus member.

Yet another aspect of the present invention is a method of winding a suture into a suture channel of a suture tray package using the above-described suture winding stylus and suture winding assembly.

These and other aspects and advantages of the present invention will become more apparent from the following description and accompanying drawings.

DETAILED DESCRIPTION OF THE INVENTION

The winding fixtures of the present invention may be used in automated suture winding machinery along with tray suture packages having doors mounted over a suture channel in the packages. The fixtures (assembly) may be made of conventional materials including, but not limited to, Aluminum 6061, 316-stainless steel, M2 high speed steel, and alloy steels and the like and combinations thereof.

Figure 1:
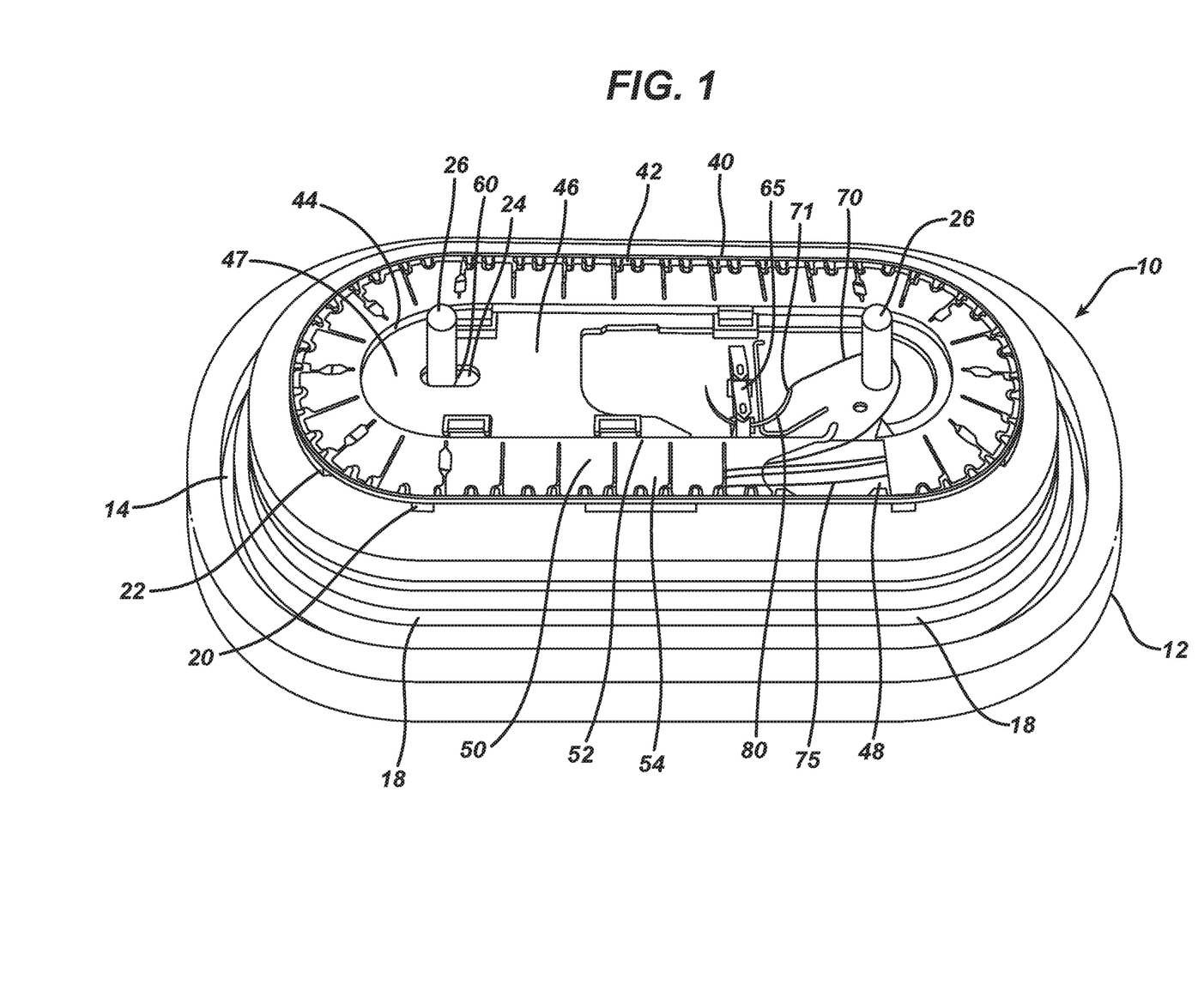
FIG. 1 is a perspective view of a suture tray package mounted in a winding nest; a surgical needle is seen mounted in a needle park and the attached surgical suture is seen to have been wound in the channel of the package.
Figure 2A:
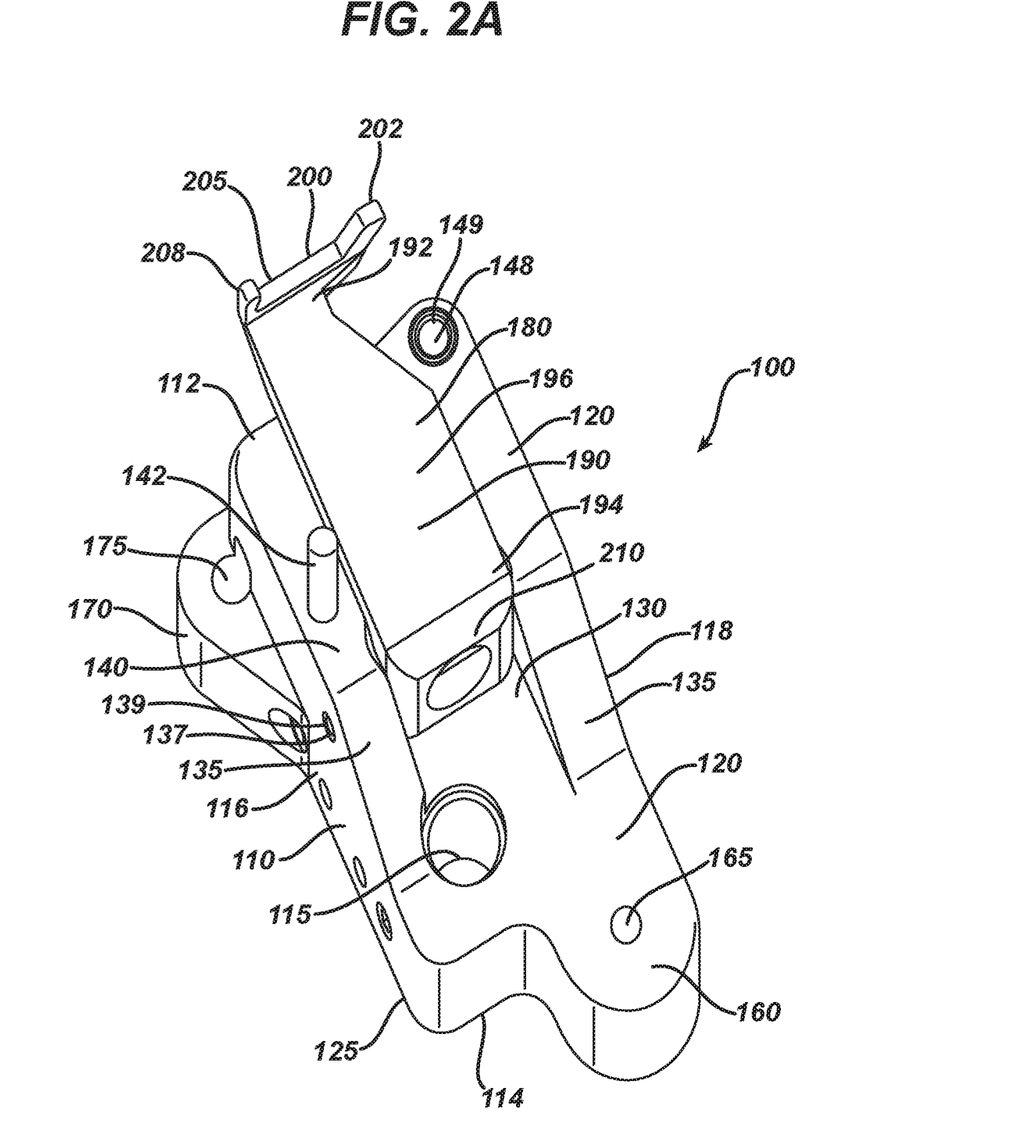
FIG. 2A is a perspective view of a winding stylus of the present invention.
Figure 2B:
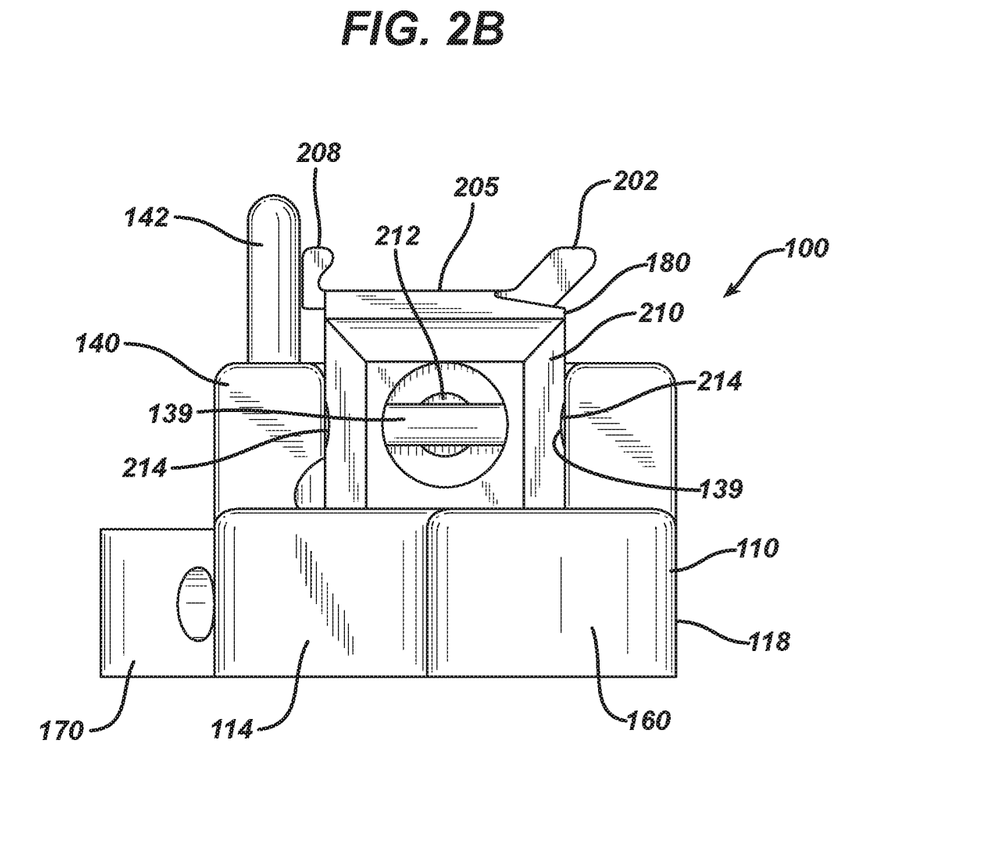
FIG. 2B is a rear view of the winding stylus of FIG. 2A.
Figure 2C:
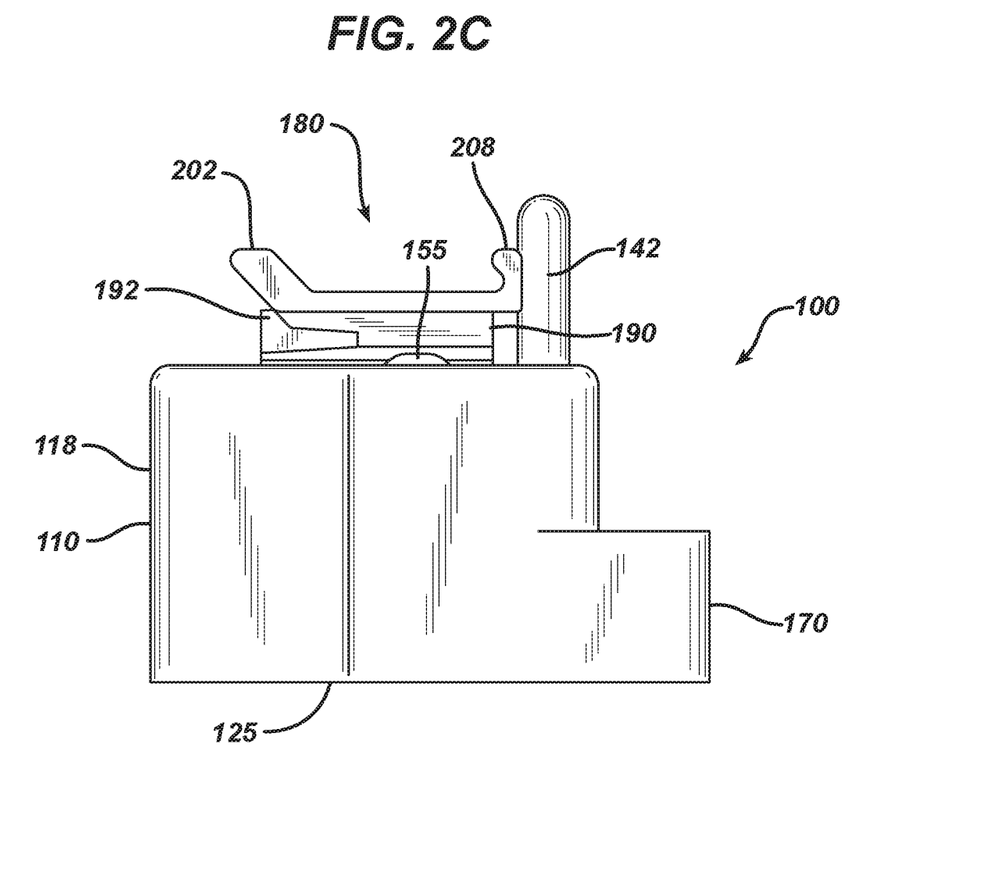
FIG. 2C is a front view of the winding stylus of FIG. 2A.
Figure 2D:
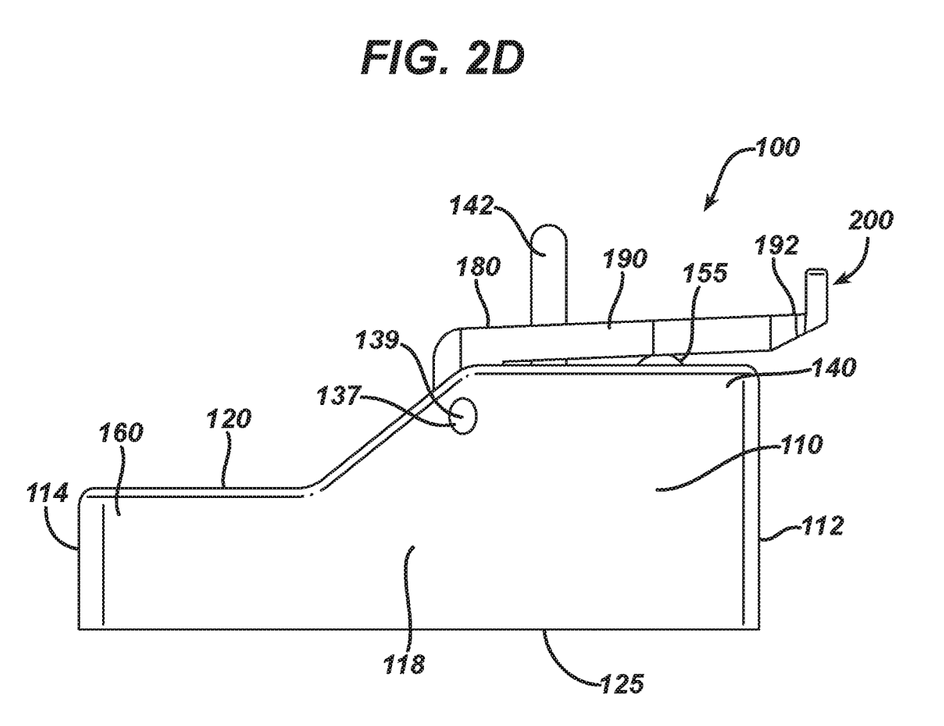
FIG. 2D is a right side view of the winding stylus of FIG. 2A.
Figure 2E:
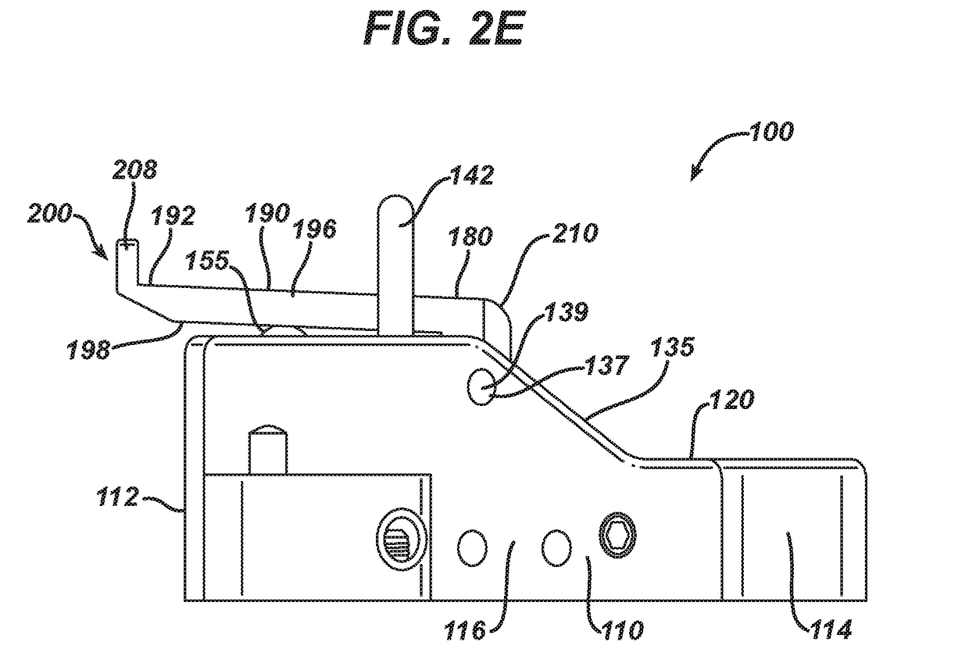
FIG. 2E is a left side view of the winding stylus of FIG. 2A.
Figure 2F:
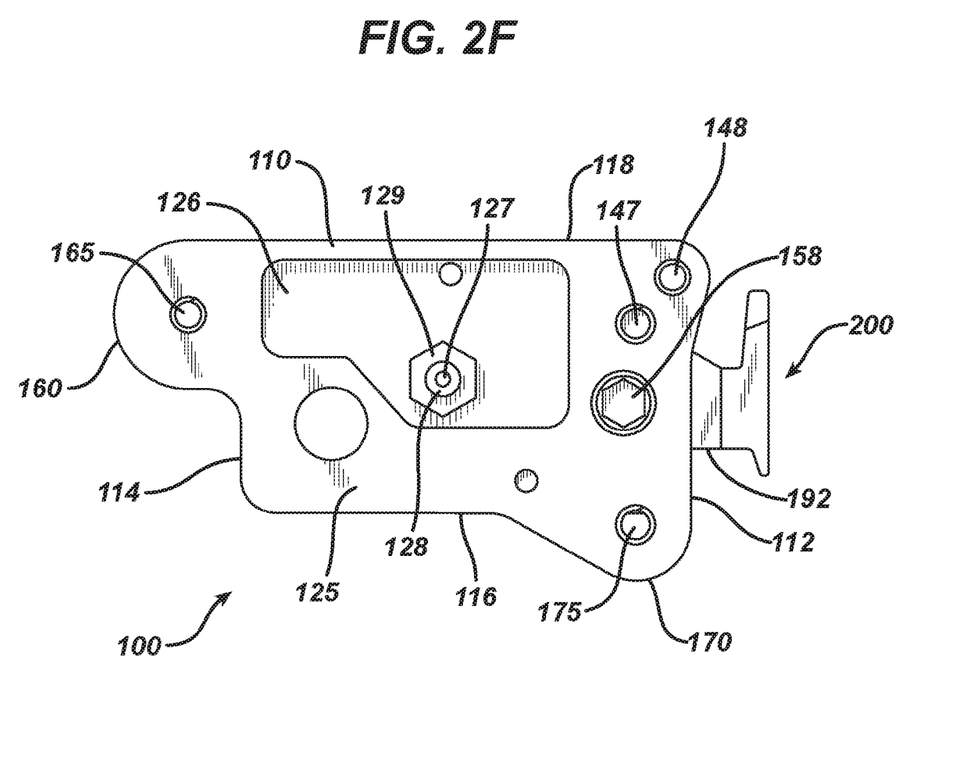
FIG. 2F is a bottom view of the winding stylus of FIG. 2A.
Figure 2G:
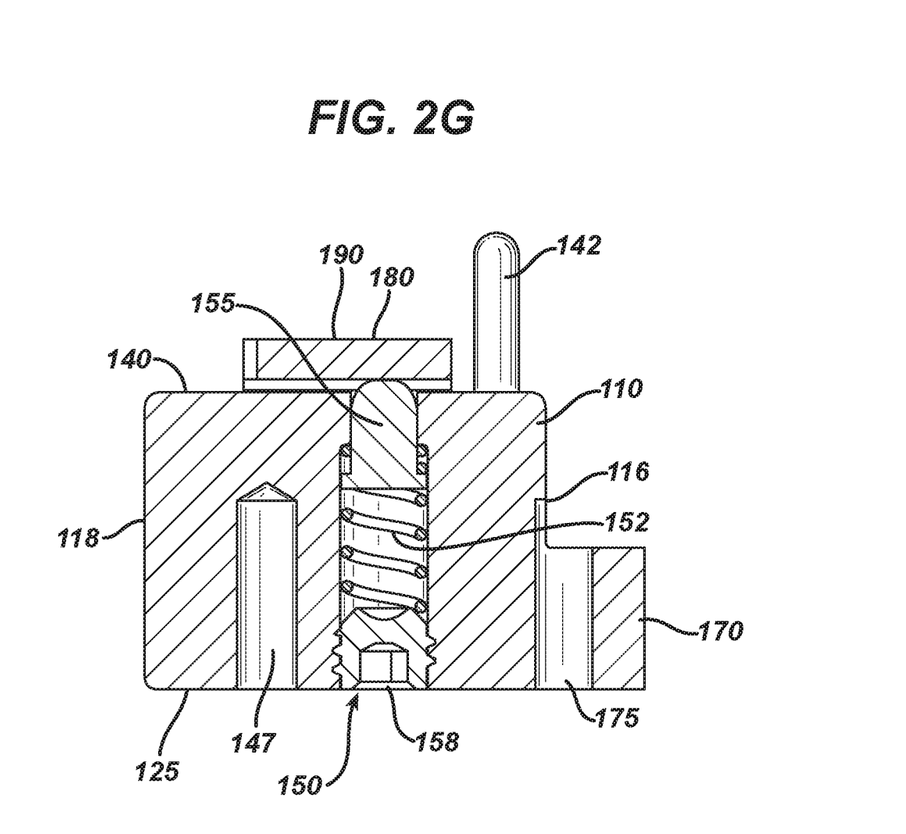
FIG. 2G is a cross-sectional view of the winding stylus of FIG. 2D.
Figure 2H:
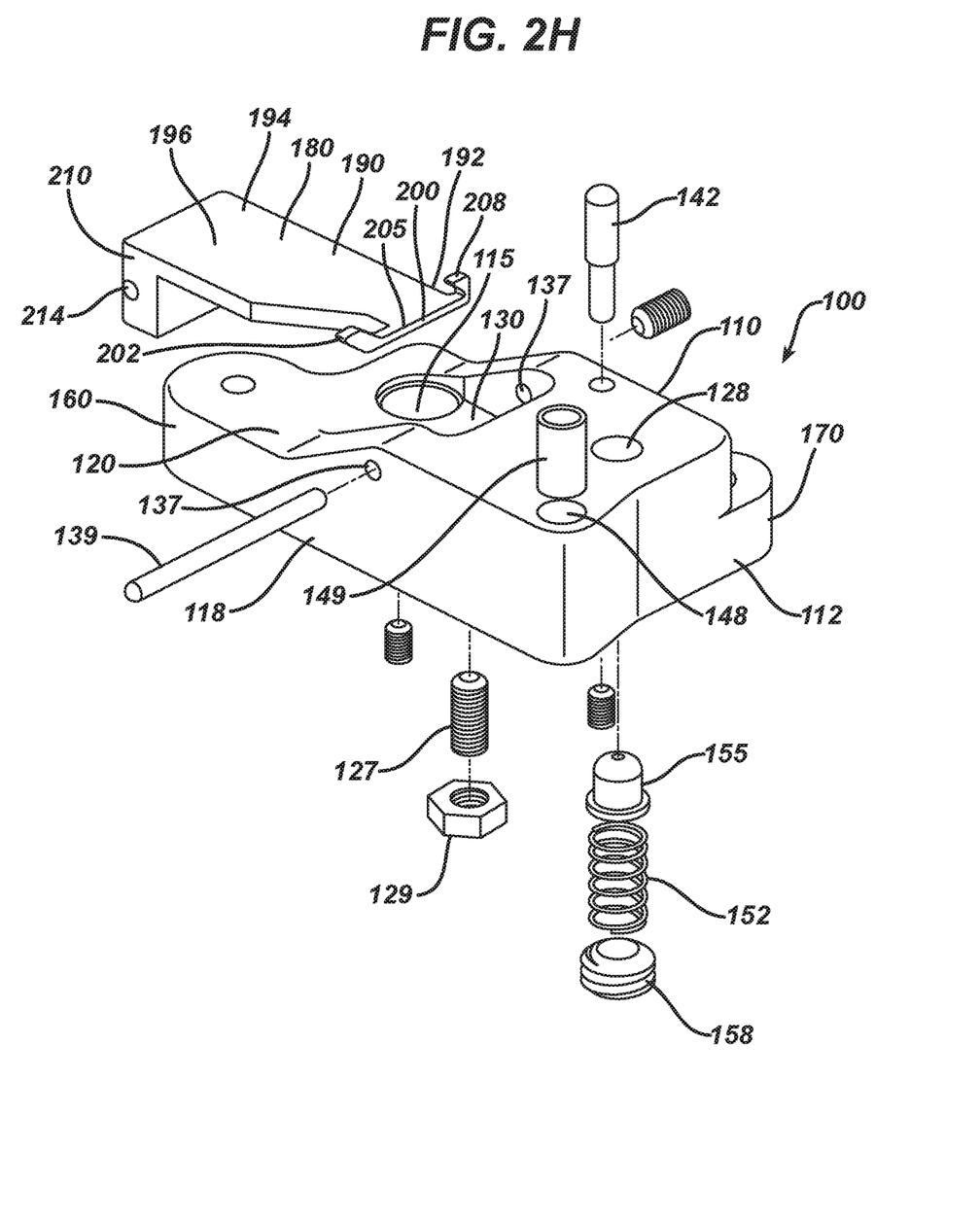
FIG. 2H is an exploded perspective view of the winding stylus of FIG. 2A.

Referring to FIG. 1, a nest member 10 and a suture tray package 40 are seen. The nest member 10 is seen is seen to have outer periphery 12 and inner raised platform section 20. The nest member 10 is also seen to have bottom tracking pin groove 14 and radial tracking pin groove 18. Platform section member 20 is seen to have oval-shaped outer periphery 22 and top surface 24. Extending upwardly from the ends of the top surface 24 are the winding pins 26. The suture tray package 40 is seen to have outer peripheral wall 42 and inner wall 44. The package 40 is also seen to have base or floor member 46 having top side 47. The section of top side 47 between outer wall 42 and inner wall 44 is seen to form the suture winding channel 48. Extending outwardly from the top of inner wall 44 are the cantilevered doors 50 having fixed ends 52 and free ends 54. The doors 50 are free to rotate about free ends 54 in response to an upward or downward force. In the at rest position, the doors 50 are seen to cover the winding channel 48. In the upward, rotated position, the doors 50 allow the winding channel 48 to be accessed. Extending through the base member 46 are the openings 60, which are aligned to receive the winding pins 26. The needle park members 65 are seen to extend up from the top side 47 and are configured to receive a surgical needle 80 mounted to a distal end 71 of surgical suture 70. The surgical suture 70 has a proximal end (not shown) contained in the winding channel 48. Surgical suture 70 is seen to have several coils 75 that have been wound into suture winding channel 48.

The stylus winding fixture 100 of the present invention is illustrated in FIGS. 2A-2H. The stylus winding fixture 100 is seen to have stylus mount base member 110. Stylus mount base member 110 is seen to have top side 120 and bottom side 125. The stylus mount base member 110 also has front side 112, rear side 114, first lateral side 116, and second opposed lateral side 118. Bearing mounting passage 115 is seen to extend through stylus mount base member 110. The stylus mount base member 110 is seen to have a stylus member mounting notch 130 on top side 120. The notch 130 is seen to be bounded by the lateral angulated sides 135 and the distal platform section 140 extending up and intersecting sides 135. Sides 135 are seen to have pin mounting holes 137 extending therethrough. The stylus mount wee pin 142 is seen to extend up from platform section 140. The passage 150 is seen to extend through platform section 140, extending from the bottom side 125 through the top side 120. Contained in the passage 150 are the compression spring 152 and the stylus mount tip 155. The spring 152 and the mount tip 155 are maintained in passage 150 by the set screw 158. It will be appreciated that although spring 152 is shown to be a compression spring, other conventional biasing members may be used. In addition, spring 152 is shown mounted in the stylus mounting base member 110, but alternatively a biasing member could be mounted in a variety of manners, for example on top of surface 120. Extending rearwardly from the rear side 114 is the bearing mounting ear 160 having opening 165. Mounting ear 170 is seen to extend laterally from lateral side 116; it is seen to have opening 175. The stylus member 180 is seen to be mounted in notch 130 by pivot pin 139. The pivot pin 139 is seen to extend through holes 137 and pin receiving openings 214 of plate member 210. The stylus member 180 is seen to have elongated member 190 having distal end 192 and proximal end 194. The elongated member 190 has top side 196 and bottom side 198. Mounted to the distal end 192 of elongated member 190 is the stylus head 200. The head 200 is seen to have angulated upwardly extending first nose member 202 and upwardly extending second heel member 208 separated by gap 205. Extending from the proximal end 194 of the elongated member 190 is the rear mounting plate member 210. Plate member 210 is seen to have an axial passage 212 and opposed pin receiving openings 214 in communication with passage 212. Also contained in the stylus mount base member 110 is the stylus mount bushing 149 contained in the opening 148 in base member 110. Contained in bottom 125 is the cavity 126. The cup point set screw 127 is engaged in screw threaded passage 128 and secured with hex nut 129. The set screw 127 is used to adjust the height of the stylus member 180 with respect to top surface 120 of the mounting base member 110 in raised platform section 140.

Figure 3:
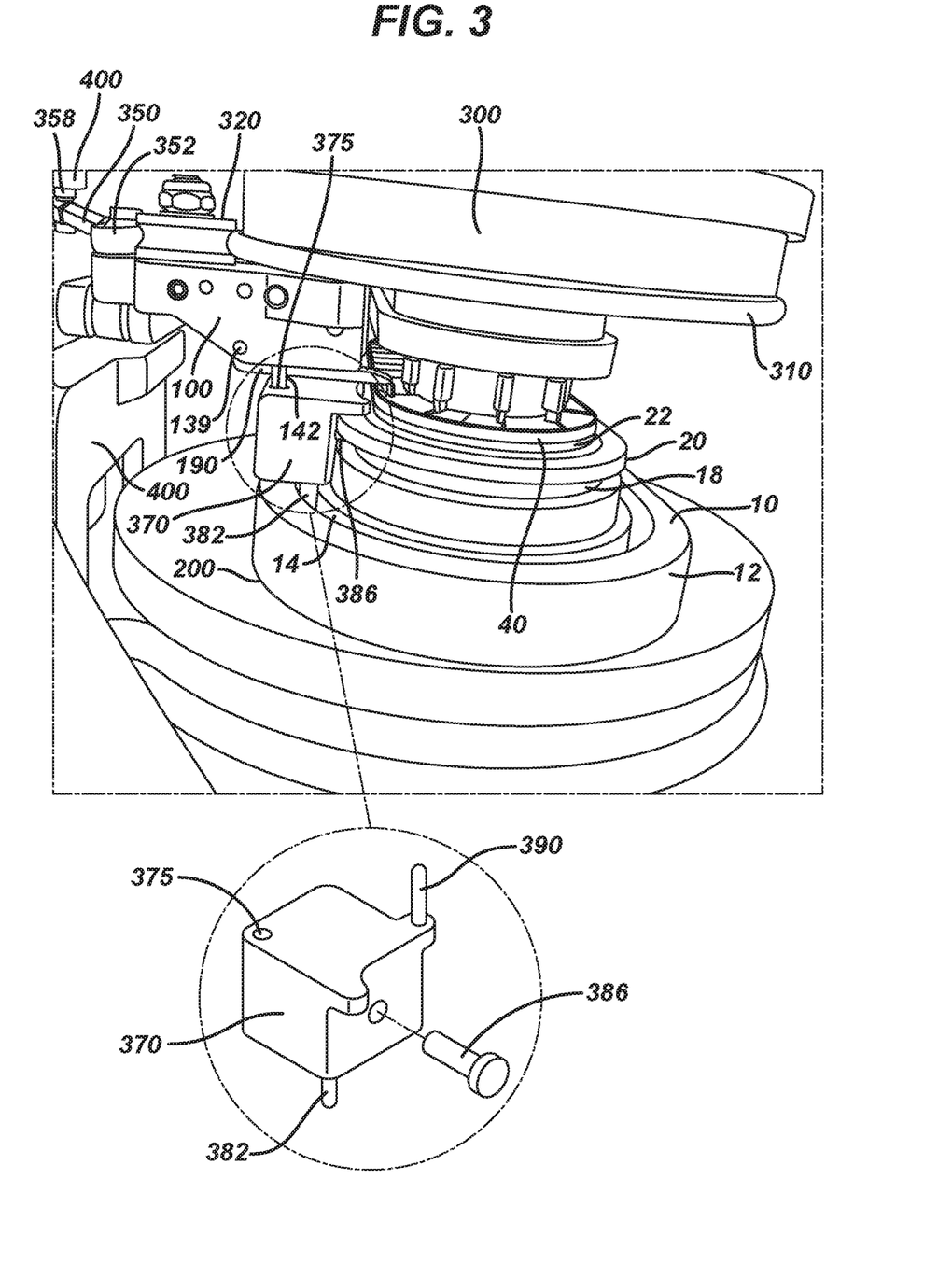
FIG. 3 is a partial perspective view of a winding head engaging a nest member and a tray package, with a novel winding stylus of the present invention engaging the winding head and the track of the tray package.
Figure 4:
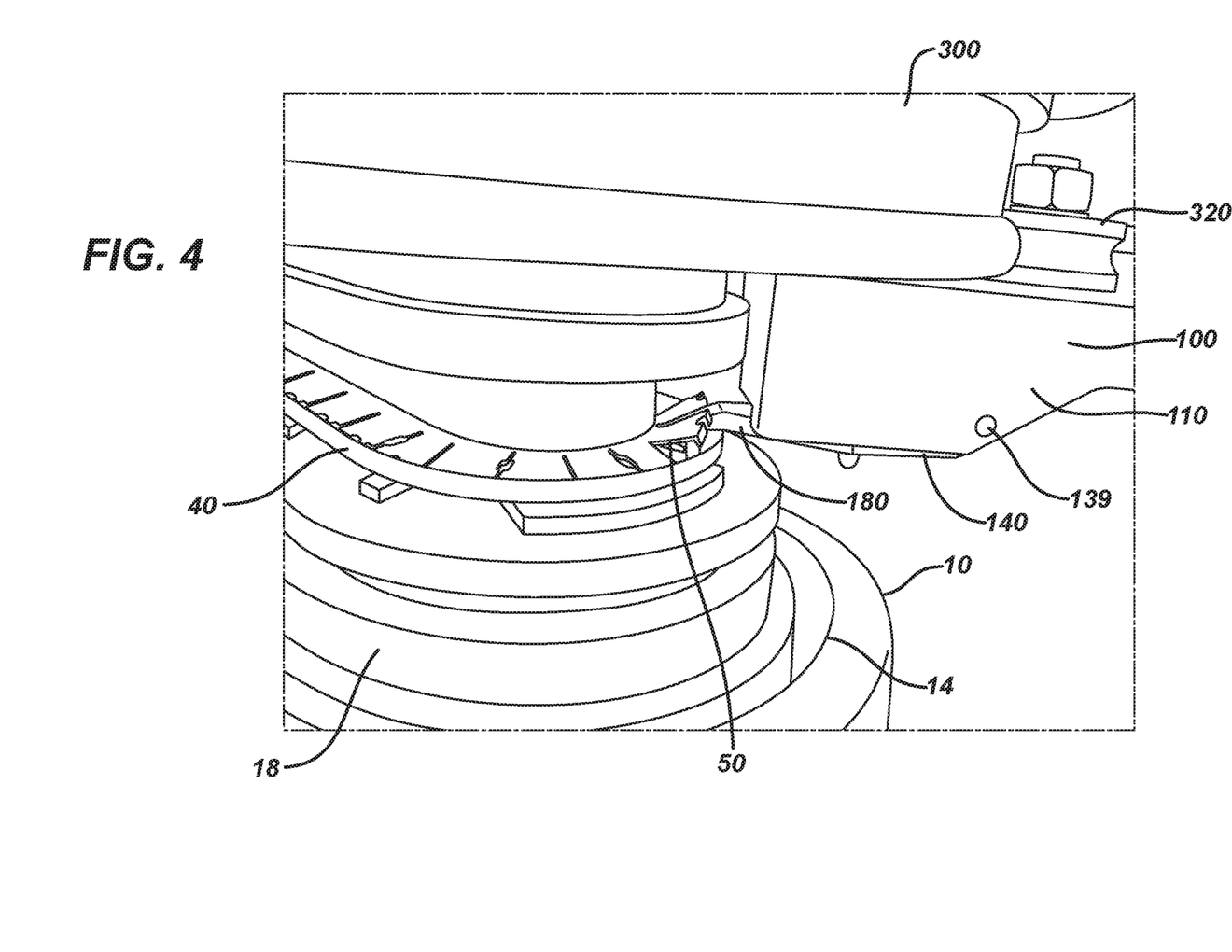
FIG. 4 is a perspective view of a winding stylus of the present invention engaging the doors covering a winding track of a suture tray package; the tray package is engaged by a winding head and a nest member.
Figure 5:
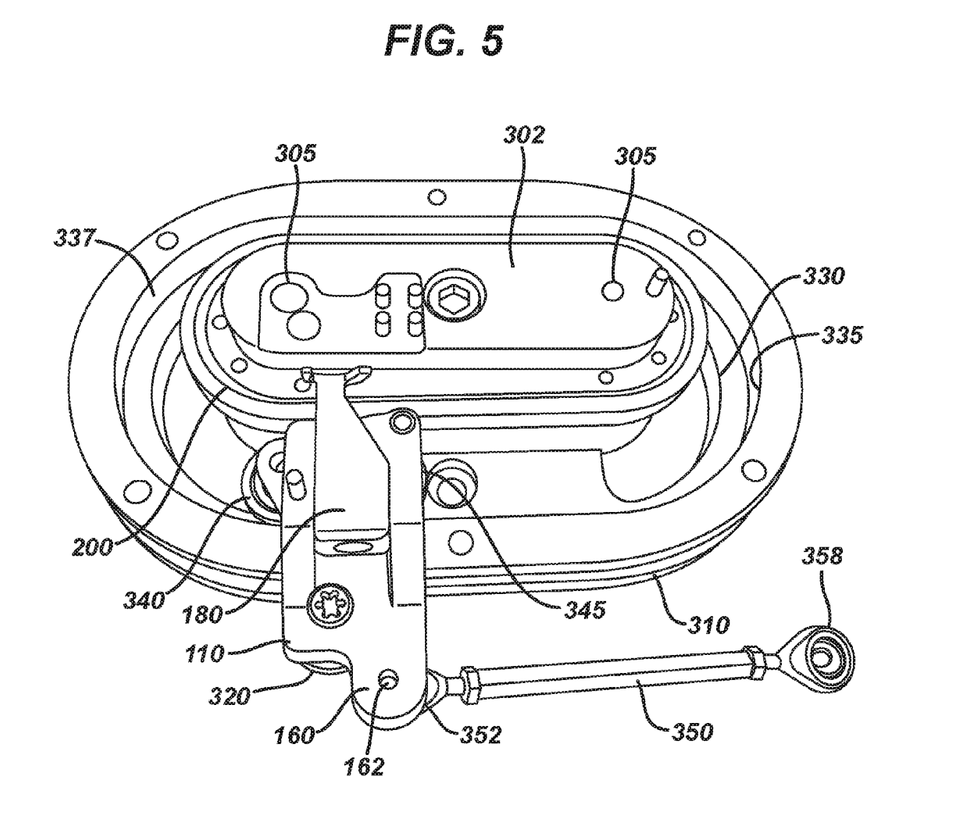
FIG. 5 is a bottom, perspective view of a winding head with a novel winding stylus of the present invention engaging an inner track wall of the winding head with the bottom of the winding stylus facing the winding head.
Figure 6:
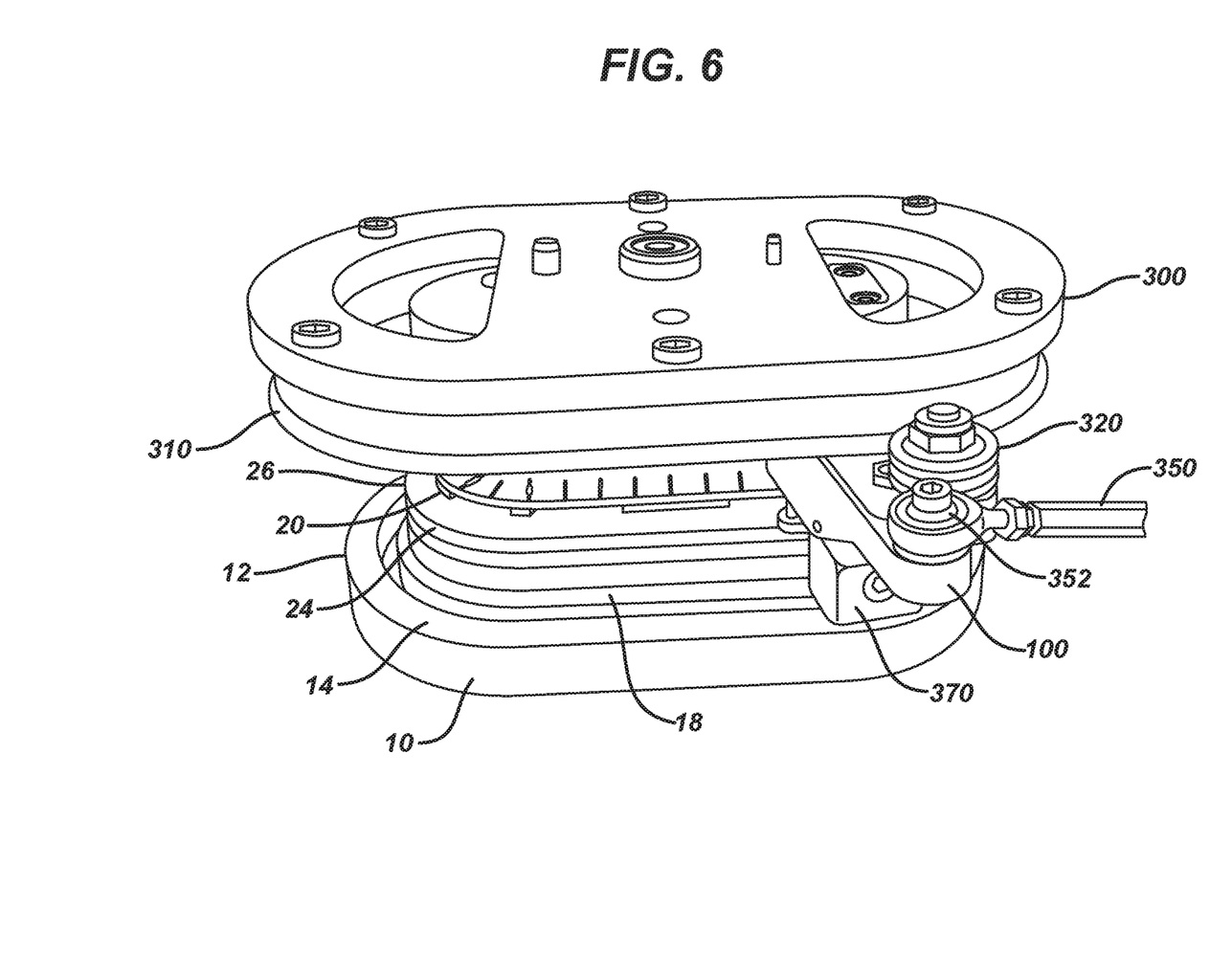
FIG. 6 is a perspective view of the novel winding stylus of the present invention mounted to the winding head of FIG. 5 and engaging a tray package in a winding nest.
Figure 7:
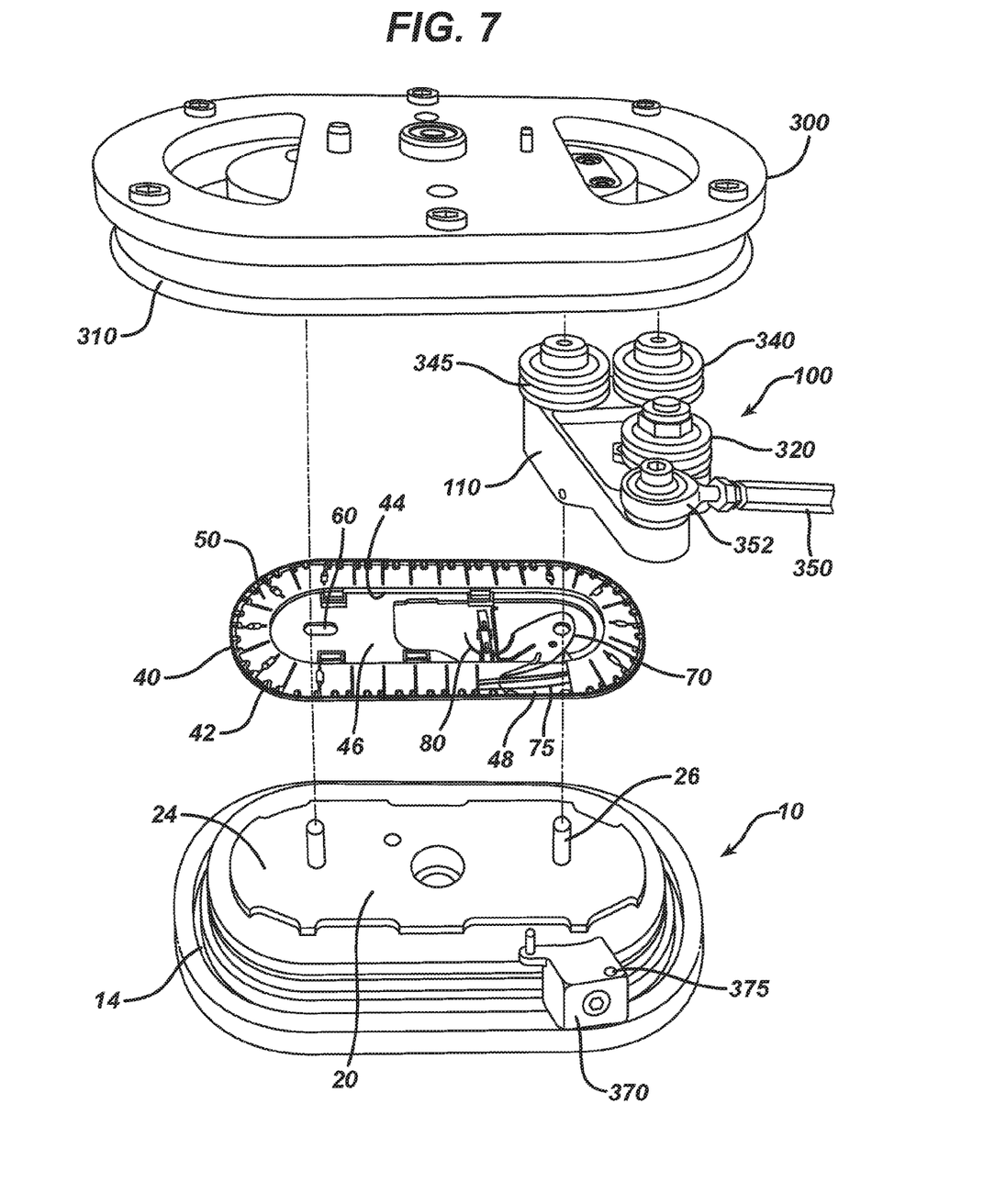
FIG. 7 is an exploded perspective view of the winding stylus of the present invention, winding head, tray package and winding nest of FIG. 6.

Referring now to FIGS. 3-6, the novel winding stylus 100 is seen mounted to winding head 300. Winding head 300 is mounted to winding head machine frame 400. The winding head has downwardly extending section 302 containing pin receiving openings 305. The winding head 300 is seen to have top outer cam track 310 which is engaged by cam follower bearing 320. Bearing 320 is seen to be mounted in opening 115. As seen in FIG. 5, the stylus 100 is engaged in the interior section 330 of head 300 by the bearings 340 and 345 that engage interior track wall 335 and inwardly extending cam member 337. Bearing 340 is seen to be mounted from the bottom side 125 of stylus mounting base member 110 in opening 175 and bearing 345 is seen to be mounted from bottom side 125 in opening 147 of the stylus base member 110. Constraining rod 350 is seen to be mounted on one end 352 to passage 165 in ear 160; the other end of the rod 358 is mounted to the winding head machine frame 400. As seen in FIGS. 3 and 6, the stylus follower member 370 is seen to be moveably mounted to the nest member 10. Follower member 370 has downwardly extending wee pin 382 that rides in groove 14 of nest member 10 and inwardly extending wee pin 386 that rides in groove 18 of nest member 10. The follower member 370 is also seen to have upwardly extending wee pin member 390 that is inserted into bushing 148 and opening 149 of stylus mounting base member 110. The follower member 370 is also seen to have top opening 375 for receiving the stylus mount wee pin 142.

For winding sutures into the tray of a tray package using the winding stylus 100 of the present invention with a suture winding assembly, a tray package 40 is place on the platform 20 of nest member 10 such that the winding pins 26 are engaged in the openings 60. A surgical needle is then mounted between the needle park members 65. The distal end 71 of attached suture 70 is then routed out from the tray package 40 in preparation for winding. Next, the winding head 300 and mounted stylus winding fixture 100 of the present invention are lowered to engage the package 40 and nest member 10. In the lowered engagement position, the winding pins 26 are engaged by the mating pin receiver openings 305, and the stylus mount wee pin 142 has engaged opening 375 of the follower member 370, while the wee pin member 390 of the follower member 370 is engaged by bushing 148 in opening 149 of the stylus mount base member 110. Additionally, the head 200 of the stylus member 180 is in engaged with the channel 48 of tray package 40, in a position to open and close doors 50.

As seen in FIG. 3, the winding head 300 has engaged nest member 10 containing tray package 40. The stylus head 200 is seen to be engaged in channel 48 of tray package 40. The suture winding head 300 is in a ready position to commence suture winding by rotating head 300, thereby causing package 40 and nest member 10 to rotate. As seen in FIG. 4, this rotation causes the stylus head 200 to open and close the doors 50 to permit insertion of the free end of the suture 70 as coils 75 are formed in channel 48.

The novel winding stylus 100 of the present invention allows a suture to be wound in channel, such as channel 48, of a tray package, such as package 40, in a consistent manner while compensating for irregularities in the package, thereby extending the life of the bearings mounted to stylus mount member 110. Other advantages of the novel stylus of the present invention having a pivotally mounted spring biased stylus member include the ability to wind sutures in a track of a tray package in a consistent manner while compensating for normal variations in tray package dimensions resulting from manufacturing processes and material variations. The novel winding styluses also compensate for movement caused by bearing wear, allowing the winding equipment to stay in service longer before a shutdown to replace bearings. These benefits are accomplished by the novel winding styluses of the present invention in the following manner. The innovative adaptive stylus 100 of the present invention resiliently maintains contact with the bottom surface of the channel 48 of tray package 40 ensuring a reliable winding process and consistent operation. Other advantages include better process capability by quality improvement on miss-wind and suture damage reduction (greater than 50% improvement), and, overall equipment efficiency (OEE) improvement by availability and yield increase. Since the novel adaptive stylus fixture of the present invention reduces the mechanical adjustment and maintenance interventions, the machine availability is increased. Also, the fixture and methods of the present invention provide winding yields that are high due to miss-wind and suture damage defect reduction. The adaptive stylus fixtures of the present invention also drive cost improvement through labor and cost reductions resulting from, among other things, less adjustments and less part replacements that are required during use.

Although this invention has been shown and described with respect to detailed embodiments thereof, it will be understood by those skilled in the art that various changes in form and detail thereof may be made without departing from the spirit and scope of the claimed invention.

I claim:

1. A suture winding stylus, comprising:
    a base member, the base member having a top side, a bottom side and opposed front and rear lateral sides; and,
    a stylus member pivotally mounted to the base member, the stylus member having a proximal end, a distal end, a top side and a bottom side;
    a stylus head member mounted to the distal end of the stylus member; and,
    a biasing element associated with the base member for engaging the stylus member.

2. The suture winding stylus of claim 1, wherein the suture winding stylus additionally comprises a bearing.

3. The suture winding stylus of claim 1, wherein the biasing element comprises a compression spring.

4. The suture winding stylus of claim 3, wherein the biasing element additionally comprises a tip member for engaging the bottom side of the stylus member.

5. The suture winding stylus of claim 1, wherein the stylus head member comprises a nose member and a heel member separated by a gap.

6. A suture winding assembly, comprising:
    a nest member for receiving a suture tray package having a winding channel:
    a winding head; and,
    a suture winding stylus engaging the winding head, the suture winding stylus comprising:
    a base member, the base member having a top side, a bottom side and opposed front and rear lateral sides; and,
    a stylus member pivotally mounted to the base member, the stylus member having a proximal end, a distal end, a top side and a bottom side; and,
    a biasing element associated with the base member for engaging the stylus member.

7. The suture winding assembly of claim 6, wherein the suture winding stylus additionally comprises a bearing.

8. The suture winding assembly of claim 6, wherein the biasing element comprises a compression spring.

9. The suture winding assembly of claim 8, wherein the biasing element additionally comprises a tip member for engaging the bottom side of the stylus member.

10. The suture winding assembly of claim 6, wherein the stylus member additionally comprises a stylus head associated with the distal end of the stylus member.

11. The suture winding assembly of claim 10, wherein the stylus head comprises a nose member and a heel member separated by a gap.

12. A method of winding a suture into a suture tray:
    mounting a suture tray having a suture channel into a nest member;
    inserting a section of a suture winding stylus into the suture channel, wherein the suture winding stylus comprises:
    a base member, the base member having a top side, a bottom side and opposed front and rear lateral sides;
    a stylus member pivotally mounted to the base member, the stylus member having a proximal end, a distal end, a top side and a bottom side; and,
    a biasing element associated with the base member for engaging the stylus member;
    engaging the nest member with a winding head causing the nest member and the suture tray to rotate with respect to the suture winding stylus, thereby causing a suture to be wound into the suture channel.

13. The method of claim 12, wherein the suture winding stylus additionally comprises a bearing.

14. The method of claim 12, wherein the biasing element comprises a compression spring.

15. The method of claim 14, wherein the biasing element additionally comprises a tip member for engaging the bottom side of the stylus member.

16. The method of claim 12, wherein the stylus member additionally comprises a stylus head associated with the distal end of the stylus member.

17. The method of claim 16, wherein the stylus head comprises a nose member and a heel member separated by a gap.

* * * * *